United States Patent
Guo et al.

(10) Patent No.: US 11,414,989 B2
(45) Date of Patent: Aug. 16, 2022

(54) OPTICAL ANALYSIS OF WELLBORE FLUID DEMULSIFIERS

(71) Applicant: Halliburton Energy Services, Inc., Houston, TX (US)

(72) Inventors: Li Guo, Humble, TX (US); Jay Paul Deville, Spring, TX (US); William Walter Shumway, Spring, TX (US); Kay Ann Galindo, Montegomery, TX (US)

(73) Assignee: Halliburton Energy Services, Inc., Houston, TX (US)

(*) Notice: Subject to any disclaimer, the term of this patent is extended or adjusted under 35 U.S.C. 154(b) by 355 days.

(21) Appl. No.: 16/614,586

(22) PCT Filed: Aug. 3, 2018

(86) PCT No.: PCT/US2018/045098
§ 371 (c)(1),
(2) Date: Nov. 18, 2019

(87) PCT Pub. No.: WO2019/055151
PCT Pub. Date: Mar. 21, 2019

(65) Prior Publication Data
US 2020/0200005 A1 Jun. 25, 2020

Related U.S. Application Data

(60) Provisional application No. 62/558,154, filed on Sep. 13, 2017.

(51) Int. Cl.
*E21B 49/08* (2006.01)
*E21B 43/38* (2006.01)
(Continued)

(52) U.S. Cl.
CPC .............. *E21B 49/08* (2013.01); *E21B 43/38* (2013.01); *G01N 21/5907* (2013.01);
(Continued)

(58) Field of Classification Search
CPC ..... E21B 43/38; E21B 49/08; G01N 21/5907; G01N 21/82; G01N 21/85; G01N 33/2823; G01N 2021/5923
See application file for complete search history.

(56) References Cited

U.S. PATENT DOCUMENTS

2003/0217971 A1 11/2003 Varadaraj et al.
2008/0149486 A1 6/2008 Greaney et al.
(Continued)

FOREIGN PATENT DOCUMENTS

WO WO 2007/096024 A1 8/2007

OTHER PUBLICATIONS

International Search Report and The Written Opinion of the International Search Authority, or the Declaration, dated Nov. 27, 2018, PCT/US2018/045098, 13 pages, ISA/KR.

*Primary Examiner* — Mark R Gaworecki
(74) *Attorney, Agent, or Firm* — Haynes and Boone, LLP

(57) ABSTRACT

Embodiments of the present disclosure provide optical methods and systems to evaluate the performance of a demulsifying agent in wellbore fluid. The present embodiments provide an optical system which scans wellbore fluid in order to detect the phase separation caused by a demulsifying agent. Using spectral data, the optical system quantifies the opacity and/or transparency of the different phases in the wellbore fluid in order to evaluate the demulsifying agent.

13 Claims, 3 Drawing Sheets

(51) Int. Cl.
  *G01N 21/85*    (2006.01)
  *G01N 21/82*    (2006.01)
  *G01N 21/59*    (2006.01)
  *G01N 33/28*    (2006.01)

(52) U.S. Cl.
  CPC ............ *G01N 21/82* (2013.01); *G01N 21/85* (2013.01); *G01N 33/2823* (2013.01); *G01N 2021/5923* (2013.01)

(56) References Cited

U.S. PATENT DOCUMENTS

| | | |
|---|---|---|
| 2010/0015720 A1 | 1/2010 | McDaniel et al. |
| 2012/0140058 A1 | 6/2012 | McDaniel et al. |
| 2013/0032736 A1* | 2/2013 | Tunheim ................ G01N 21/85 250/564 |

* cited by examiner

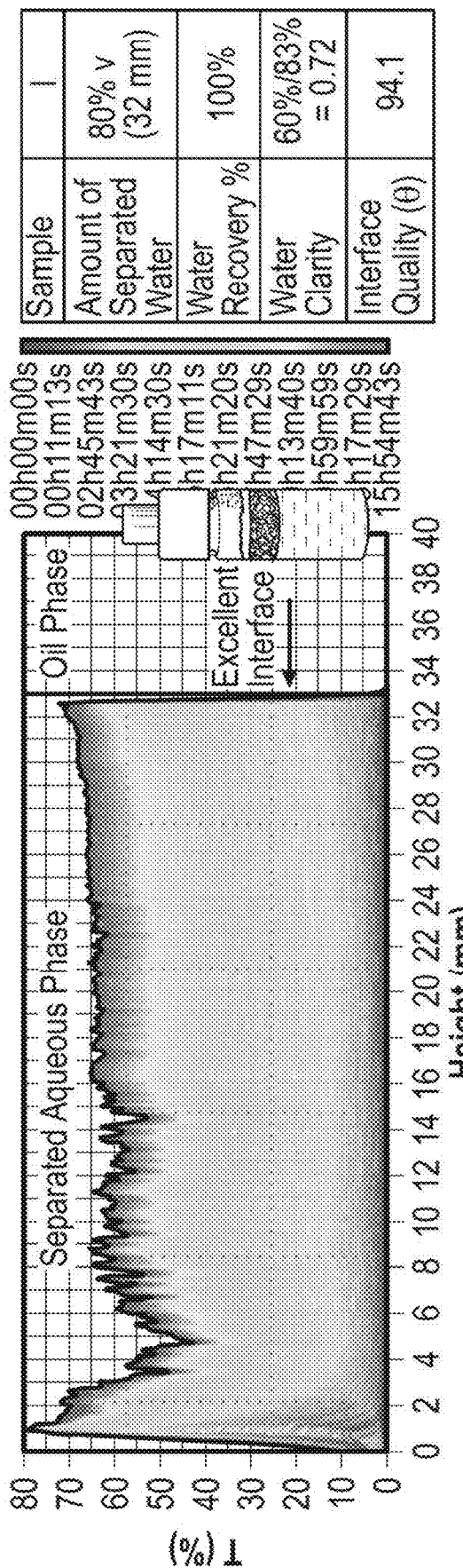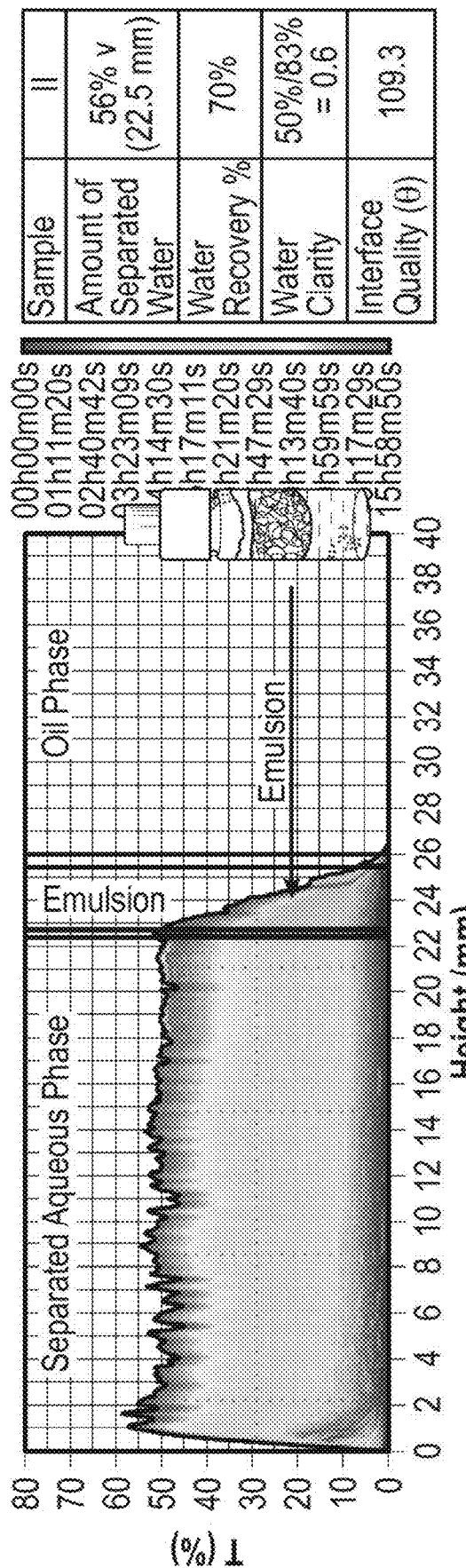
FIG. 3A
FIG. 3B

OPTICAL ANALYSIS OF WELLBORE FLUID DEMULSIFIERS

PRIORITY

The present application is an International Patent Application of U.S. Provisional Application No. 62/558,154, filed on Sep. 13, 2017, entitled "OPTICAL ANALYSIS OF WELLBORE FLUID DEMULSIFIERS," the benefit of which is claimed and the disclosure of which is incorporated herein by reference in its entirety.

FIELD OF THE DISCLOSURE

The present disclosure relates generally to hydrocarbon recovery and, more specifically, to an optical analysis method to perform separation tests on emulsified wellbore fluid.

BACKGROUND

In order to conduct downhole completion operations, special fluids must be used downhole during drilling of the wellbore. The wellbore fluids typically include a completion fluid and a drill-in fluid in order to maintain fluid weighting requirements used to prevent blowouts of the wellbore. An emulsification agent is also added to the completion and drill-in fluids in order to ensure the fluid remains homogenous during the completion process. Once the wellbore is completed and production begins, the completion and drill-in fluids are produced from the wellbore along with the hydrocarbons, brine, etc. from the reservoir, also referred to as "flow-back fluid." Therefore, the flow-back fluid must then be demulsified at the surface using some form of demulsifying agent in order to separate the hydrocarbons from the other components.

In order to identify suitable demulsification agents, the conventional approach involves a demulsification test (e.g., a Flow-to-Host bottle test). Here, the flow-back fluid is introduced into one or more test bottles along with candidate demulsification agents. The bottles are then shook by hand and allowed to sit for a prolonged period of time (e.g., 2 minutes to 16 hours), over which they are visually inspected to determine when separation of the aqueous and oil phases occur. The technician visually observing the test bottles must make a judgment call as to which test bottle (and corresponding candidate demulsification agent) looks the best based upon its separation efficiency (e.g., thickness of phases, aqueous phase clarity, etc.). Once the best demulsification agent is identified, it is used during the completion operation. However, the conventional approach of identifying optimal agents can be very subjective and time consuming.

Recently, Flow-to-Refinery operations have begun being conducted in the oil and gas industry. A Flow-to-Refinery operation is one in which drill-in and/or completion fluid used to complete the well is flowed back from the well and is transported directly from the wellbore to the refinery, typically via pipeline. This fluid may then be referred to as a flow back fluid. Unlike conventional production operations, there is no intermediate treatment or separation of the flow-back fluids between the wellbore and refinery in a Flow-to-Refinery operation, which can lead to clogging and potential damage to refineries.

BRIEF DESCRIPTION OF THE DRAWINGS

FIGS. 3A and 3B show an illustrative analysis of spectral data, according to an illustrative embodiment of the present disclosure.

DESCRIPTION OF ILLUSTRATIVE EMBODIMENTS

Figure 1:
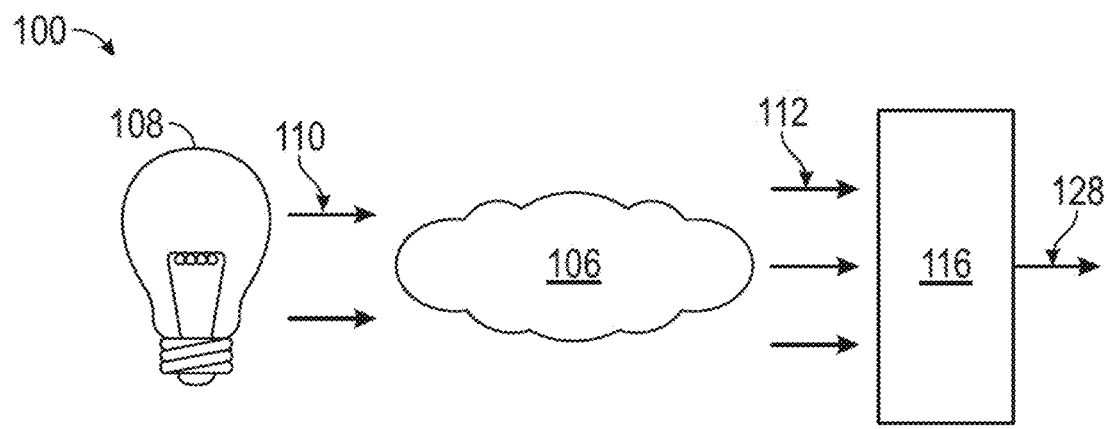
FIG. 1 is a block diagram of an optical system 100 to evaluate performance of a demulsifying agent in wellbore, according to certain illustrative embodiments of the present disclosure.

Illustrative embodiments and related methods of the present disclosure are described below as they might be employed in optical methods and systems to evaluate the performance of a demulsifying agent in wellbore fluid. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, illustrative embodiments of the present disclosure provide optical methods and systems to evaluate the performance of a demulsifying agent in wellbore fluid. The present embodiments provide an optical device or system which scans wellbore fluid in order to detect the phase separation caused by a demulsifying agent. The optical system quantifies the opacity and/or transparency of the different phases in the wellbore fluid in order to evaluate the demulsifying agent. The optical system may compare candidate demulsifying agents and their corresponding kinetics of phase separation (i.e., how fast or slow separation occurs—in other words, the speed at which phase separation occurs) in order to determine the optimal demulsifying agent. Alternatively, the optical system may analyze demulsifying agents in real-time in order to monitor demulsification at a well site (e.g., during a Flow-to-Refinery operation). Accordingly, the illustrative embodiments of the present disclosure enable measurement of the efficiency of additives used for demulsification, as it scans and identifies instabilities much more rapidly and accurate that conventional human-eye identification. Moreover, the optical method is objective, thus enabling efficient sample comparison.

In a generalized optical method, electromagnetic radiation optically interacts with wellbore fluid (e.g., flow-back fluid) to produce sample-interacted light. The wellbore fluid includes an aqueous and oil phase, as well as the demulsifying agent. The sample-interacted light is then caused to optically interact with an optical detector in order to detect separation of the aqueous and oil phases of the wellbore fluid caused by the demulsifying agent. Thereafter, based upon the detected phase separation, the optical system evaluates the performance of the demulsifying agent. This generalized method may be used to identify demulsifying agents necessary for a given completion operation before the operation begins. Alternatively, the method may be used in real-time at the well site for identification or analysis of demulsifying agents, as well as to monitor demulsification of flow-back fluids from the wellbore.

FIG. 1 is a block diagram of an optical system 100 to evaluate performance of a demulsifying agent in wellbore, according to certain illustrative embodiments of the present disclosure. Optical systems as described herein may take various forms, such as for example, a spectroscopy or other optical device providing analysis of samples. One example of an optical device which may be employed in embodiments of the present disclosure are the Turbiscan™ optical analyzers, commercially offered by Formulaction SA of L'Union France. Those ordinarily skilled in the art having the benefit of this disclosure will realize these and other optical devices, as well as their associated spectral analysis techniques, may be used in the present disclosure.

Nevertheless, with reference to FIG. 1, an electromagnetic radiation source 108 may be configured to emit or otherwise generate electromagnetic radiation 110. As understood in the art, electromagnetic radiation source 108 may be any device capable of emitting or generating electromagnetic radiation. For example, electromagnetic radiation source 108 may be a light bulb, light emitting device, laser, blackbody, photonic crystal, or X-Ray source, natural luminescence, etc. In one embodiment, electromagnetic radiation 110 may be configured to optically interact with the wellbore fluid sample 106 to thereby generate sample-interacted light 112. Wellbore fluid sample 106 may be any desired sample, such as, for example, a flow-back fluid (liquid or gas), solid substance or material such as, for example, hydrocarbons. While FIG. 1 shows electromagnetic radiation 110 as passing through or incident upon the sample 106 to produce sample-interacted light 112 (i.e., transmission or fluorescent mode), it is also contemplated herein to reflect electromagnetic radiation 110 off of the sample 706 (i.e., reflectance mode) or backscatter, such as in the case of a sample 106 that is translucent, opaque, or solid, and equally generate the sample-interacted light 112.

In the illustrated example, sample 106 is wellbore fluid comprising an aqueous/water phase, oil phase, emulsifying agent, and a demulsifying agent. Examples of demulsifying agents include, for example, TRETOLITE™ or BREAXIT™. Sample 106 may introduced to optical device 100 in a variety of ways. For example, if analysis of candidate demulsifying agents is being conducted before a completion operation, wellbore fluid 106 may be introduced within a test bottle or other testing compartment. Alternatively, if analysis of a demulsifying agent is desired in real-time at the well site (e.g., in a Flow-to-Refinery operation), the optical device 100 may be positioned in-line of the wellbore and flow-back fluid such that the flow-back fluid is analyzed in real-time. In such an embodiment, optical device 100 may be placed along a pipe or other transfer means of the flow-back fluid from the wellbore such that a fluid sample is withdrawn from the flow, deposited inside a testing chamber, and analyzed accordingly by optical device 100. Accordingly, the performance of a demulsifying agent may be monitored at the well site and/or the chemical makeup of the demulsifying agent may be altered as necessary at the well site in real-time.

With reference back to FIG. 1, after being illuminated with electromagnetic radiation 110, sample 106 containing wellbore fluid produces an output of electromagnetic radiation (sample-interacted light 112, for example). Sample-interacted light 112 contains spectral information of the wellbore fluid sample 106 used to optically quantify the opacity or transparency of the phases. In alternate embodiments, different demulsifying agents may be introduced simultaneously into other wellbore fluid samples and analyzed accordingly. The kinetics, or speed, of separation of the different samples may then be compared to determine the optimal performing demulsification agent.

Although not shown, optical device 100 may be coupled to a remote power supply, while in other embodiments optical device 100 comprises an on-board battery. Optical device 100 may also comprise a signal processor (not shown), communications module (not shown) and other circuitry necessary to achieve the objectives of the present disclosure, as will be understood by those ordinarily skilled in the art having the benefit of this disclosure. It will also be recognized that the software instructions necessary to carry out the objectives of the present disclosure may be stored within storage located on optical device 100 or loaded into that storage from a CD-ROM or other appropriate storage media via wired or wireless methods.

Alternatively, however, the processor may be located remotely from optical device 100. In such embodiments, a communications link provides a medium of communication between the processor and optical device 100. The communications link may be a wired link, such as, for example, a fiber optic cable. Alternatively, however, the link may be a wireless link. In certain illustrative embodiments, the signal processor controls operation of optical device 100. Optical device 100 may also include a transmitter and receiver (transceiver, for example) (not shown) that allows bi-directional communication over a communications link in real-time. In certain illustrative embodiments, optical device 100 will transmit all or a portion of the spectral data of fluid sample 106 to a remote processor for further analysis. However, in other embodiments, such analysis is completely handled by optical device 100 and the resulting data is then transmitted remotely for storage or subsequent analysis. In either embodiment, the processor handling the computations may, for example, analyze the spectral data, or perform simulations based upon the spectral data, as will be readily understood by those ordinarily skilled in the art having the benefit of this disclosure.

Still referring to the illustrative embodiment of FIG. 1, sample-interacted light 112 is then directed to one or more detectors 116, which may be any device capable of detecting electromagnetic radiation, and may be generally characterized as an optical transducer. For example, detector 116 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, local or distributed optical fibers, and/or combinations thereof, or the like, or other detectors known to those ordinarily skilled in the art.

Detector 116 is further configured to produce an output signal 128 in the form of a voltage that corresponds to the spectral data of sample 106, which is then used to quantify the opacity or transparency of the aqueous and oil phases of the wellbore fluid. As stated, embodiments of the present disclosure enable replacement of conventional bottle testing with an efficient optical analysis device and method utilizing optical scanning and one or more detector(s) in, for example, transmission or backscattering modes. Detection of phase separation is therefore much faster and objective than conventional visual observation. Through analysis of spectral data, the opacity or transparency of the phases can be quantified optically and not left to human appreciation, and different samples can be easily compared via kinetics of phase separation. The optical method enables measurement of the efficiency of additives used for demulsification, as the optical device sees instabilities much more rapidly and accurately than the eye.

Figure 2:
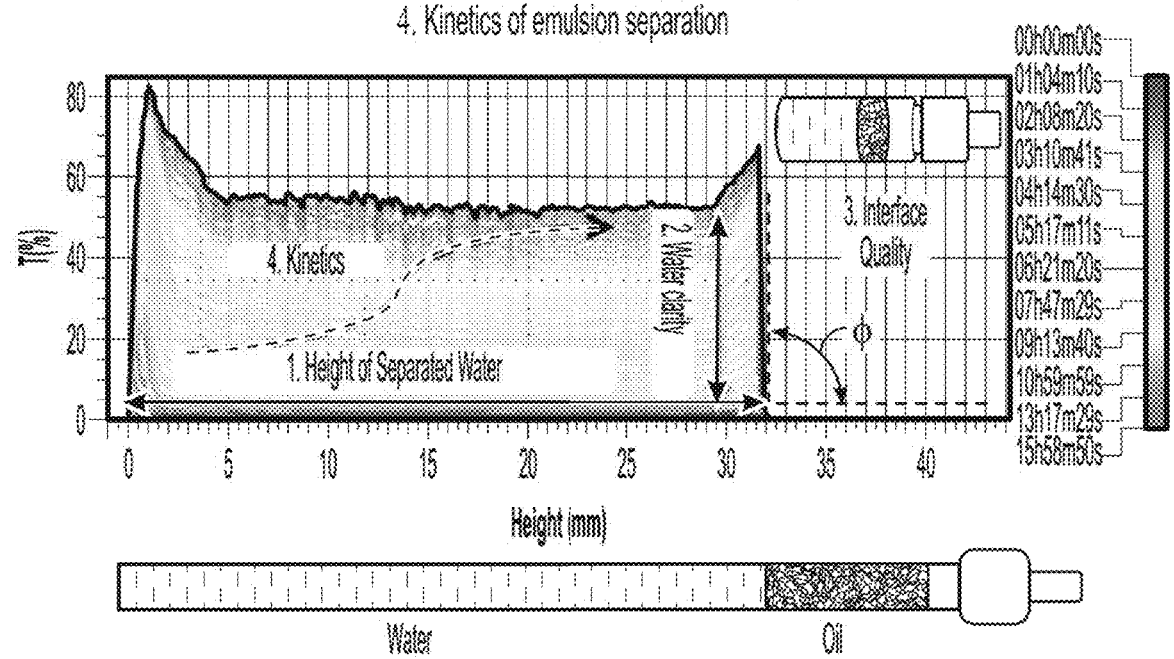
FIG. 2 is a plot showing an illustrative data analysis for an optical device, as described herein.

FIG. 2 is a plot showing an illustrative data analysis for an optical device, as described herein. According to one illustrative embodiment, based on the spectral data in sample-interacted light 112 (e.g., transmission, reflection, backscattering data, etc.), each wellbore fluid sample is presented by four data matrixes, including: (1) amount of water separated (water recovery %), (2) water clarity, (3) phase interface quality, and (4) separation kinetics (how fast or slow phase separation occurs). In this example, the plot of FIG. 2 has a Y-axis that shows the % of light transmission, or T (%), as this example shows the optical device in transmission mode, while the X-axis corresponds to the height of the tube in mm. As identified in the plot, the height of the separated water corresponds to the width of T peak. The clarity of the separated water corresponds to height of T peak. The phase separation quality corresponds to the phase interface angle φ. Lastly, the speed at which the phase separation occurs is the separation kinetics.

During the optical analysis process, the data obtained by the processor of optical device 100 is used to generate the data T (%) (because in this example optical device 100 is operating in transmission mode). Alternatively, as previously stated, other optical techniques may be used such a reflection or backscatter modes. Using the T (%) data, optical device 100 then generates a plot such as illustrated in FIG. 2, from which the amount of separated water can be determined using the width of T peak, the clarity of the separated water can be determined using the height of T peak, and the phase separation quality can be determined using the interface angle φ. Also, using time-lapse T (%) data, optical device 100 may also determine the speed at which the separation occurs. Calculation and analysis of the matrix data can be performed completely by optical device 100, or a technician may perform one or more of these calculations. Nevertheless, once all the matrix data is obtained, the data is then analyzed to determine the optimal demulsification agent.

FIGS. 3A and 3B show an illustrative analysis of the matrix data, according to an illustrative embodiment of the present disclosure. In one example, the ideal wellbore fluid sample would have 100% water recovery with an index of 1 for water clarity and the interface angle in the graph would be 90 degrees. As can be seen, FIG. 3A shows a good demulsifying agent, while FIG. 3B shows a poor demulsifying agent. The quantification of the graphs is shown to the right of each. Note the water clarity refers to how well the light transmits (T (%)) through the sample vs. clear water, and the interface quality refers to how close the phase interface is to 90 degrees. The water recovery % is determined by first determining the width of the transmission peak corresponding to the transmitted light, which gives the amount of separated water in the test tube. Second, the width of the transmission peak region is divided by what the width of the same region would be if no oil based mud was added.

Figure 4:
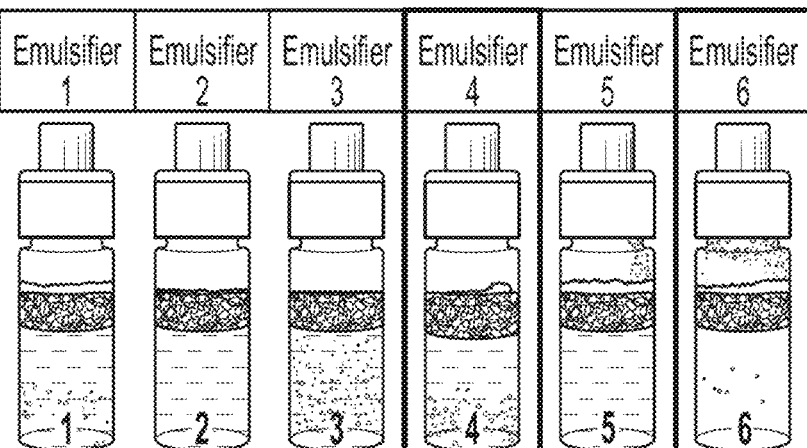
FIG. 4 shows the testing results obtained using the present disclosure.

During testing of the present disclosure, six samples were evaluated using the illustrative methods described herein. The samples were scanned by the optical device after the samples were treated with demulsification agents at 60 C for 16 hours. Based on the quantitative analysis, each sample was presented by three factors (water recovery %, water clarity, phase interface quality). By evaluation of three factors, two candidate demulsifying agent samples were identified the lead candidates. FIG. 4 shows the results of the testing. As can be seen, the optimal emulsifiers identified in the testing were #4 and #6.

Figure 5:
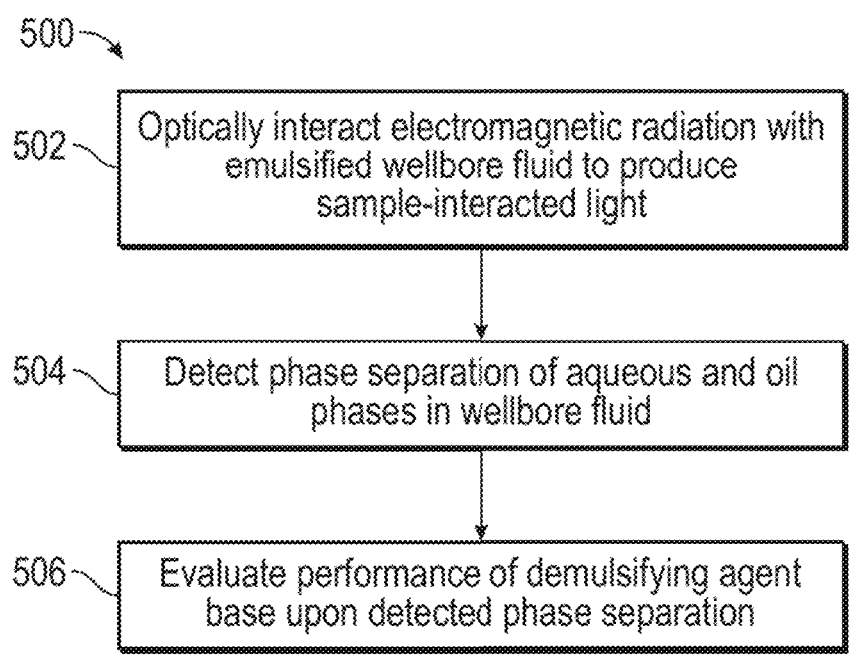
FIG. 5 is a flow chart of a method for evaluating performance of a demulsifying agent in wellbore fluid, according to certain illustrative methods of the present disclosure.

FIG. 5 is a flow chart of a method 500 for evaluating performance of a demulsifying agent in wellbore fluid, according to certain illustrative methods of the present disclosure. An optical computing device as described herein is utilized to perform method 500. In block 502, electromagnetic radiation of the optical device is optically interacted with emulsified wellbore fluid to produce sample-interacted light. The wellbore fluid is comprised of an aqueous phase, oil phase, and demulsifying agent. At block 504, the sample-interacted light then optically interacts with the detector of the optical device to thereby detect separation of the aqueous and oil phases of the wellbore fluid, using the techniques described herein. At block 506, the performance of the demulsifying is then analyzed and determined based upon the detected phase separation, again using the methods described herein.

Embodiments and methods described herein further relate to any one or more of the following paragraphs:

1. An optical method to evaluate performance of a demulsifying agent in wellbore fluid, the method comprising optically interacting electromagnetic radiation with an emulsified wellbore fluid to produce sample-interacted light, the wellbore fluid comprising an aqueous phase, oil phase, and demulsifying agent; optically interacting the sample-interacted light with an optical detector to thereby detect separation of the aqueous and oil phases of the wellbore fluid; and based upon the detected phase separation, evaluating the performance of the demulsifying agent.

2. The optical method as defined in paragraph 1, wherein evaluating the performance of the demulsifying agent comprises determining one or more of an amount of separated water; a clarity of the separated water; an interface angle which reflects a phase separation quality; a water recovery percentage; and a speed of the phase separation.

3. The optical method as defined in paragraphs 1 or 2, wherein the optical method is performed before a wellbore completion operation; and the method further comprises selecting a demulsifying agent for use in the wellbore completion operation based upon the performance evaluation.

4. The optical method as defined in any of paragraphs 1-3, wherein the optical method is performed in real-time using an optical device positioned at a wellbore, the optical device being positioned in-line of the wellbore such that the optical device receives flow back fluid from the wellbore.

5. The optical method as defined in any of paragraphs 1-4, further comprising altering a chemical makeup of the demulsifying agent in real-time based upon the performance of the demulsifying agent.

6. The optical method as defined in any of paragraphs 1-5, wherein the method is performed during a Flow-to-Refinery operation.

7. The optical method as defined in any of paragraphs 1-6, further comprising based upon the performance evaluation, selecting a demulsifying agent for use in a wellbore operation; and demulsifying fluid produced by the wellbore operation using the demulsifying agent.

8. An optical system to evaluate performance of a demulsifying agent in wellbore fluid, the system comprising a user interface; and processing circuitry communicably coupled to the user interface and configured to execute instructions to cause the system to perform operations comprising optically interacting electromagnetic radiation with an emulsified wellbore fluid to produce sample-interacted light, the wellbore fluid comprising an aqueous phase, oil phase, and demulsifying agent; optically interacting the sample-interacted light with an optical detector to thereby detect separation of the aqueous and oil phases of the wellbore fluid; and based upon the detected phase separation, evaluating the performance of the demulsifying agent.

9. The optical system as defined in paragraph 8, wherein evaluating the performance of the demulsifying agent comprises determining one or more of an amount of separated water; a clarity of the separated water; an interface angle which reflects a phase separation quality; a water recovery percentage; and a speed of the phase separation.

10. The optical system as defined in paragraphs 8 or 9, wherein the operations are performed before a wellbore completion operation; and the operations further comprise selecting a demulsifying agent for use in the wellbore completion operation based upon the performance evaluation.

11. The optical system as defined in any of paragraphs 8-10, wherein the operations are performed in real-time using an optical device positioned at a wellbore, the optical device being positioned in-line of the wellbore such that the optical device receives flow back fluid from the wellbore.

12. The optical system as defined in any of paragraphs 8-11, wherein the operations further comprise altering a chemical makeup of the demulsifying agent in real-time based upon the performance of the demulsifying agent.

13. The optical system as defined in any of paragraphs 8-12, wherein the optical system is integrated into a Flow-to-Refinery system.

Although various embodiments and methods have been shown and described, the disclosure is not limited to such embodiments and methods and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. An optical method to evaluate performance of a demulsifying agent in wellbore fluid, the method comprising:
   optically interacting electromagnetic radiation with an emulsified wellbore fluid to produce sample-interacted light, the wellbore fluid comprising an aqueous phase, oil phase, and demulsifying agent;
   optically interacting the sample-interacted light with an optical detector to thereby detect separation of the aqueous and oil phases of the wellbore fluid; and
   based upon the detected phase separation, evaluating the performance of the demulsifying agent.

2. The optical method as defined in claim 1, wherein evaluating the performance of the demulsifying agent comprises determining one or more of:
   an amount of separated water;
   a clarity of the separated water;
   an interface angle which reflects a phase separation quality;
   a water recovery percentage; and
   a speed of the phase separation.

3. The optical method as defined in claim 1, wherein:
   the optical method is performed before a wellbore completion operation; and
   the method further comprises selecting a demulsifying agent for use in the wellbore completion operation based upon the performance evaluation.

4. The optical method as defined in claim 1, wherein the optical method is performed in real-time using an optical device positioned at a wellbore, the optical device being positioned in-line of the wellbore such that the optical device receives flow back fluid from the wellbore.

5. The optical method as defined in claim 4, further comprising altering a chemical makeup of the demulsifying agent in real-time based upon the performance of the demulsifying agent.

6. The optical method as defined in claim 1, wherein the method is performed during a Flow-to-Refinery operation.

7. The optical method as defined in claim 1, further comprising:
   based upon the performance evaluation, selecting a demulsifying agent for use in a wellbore operation; and
   demulsifying fluid produced by the wellbore operation using the demulsifying agent.

8. An optical system to evaluate performance of a demulsifying agent in wellbore fluid, the system comprising:
   a user interface; and
   processing circuitry communicably coupled to the user interface and configured to execute instructions to cause the system to perform operations comprising:
      optically interacting electromagnetic radiation with an emulsified wellbore fluid to produce sample-interacted light, the wellbore fluid comprising an aqueous phase, oil phase, and demulsifying agent;
      optically interacting the sample-interacted light with an optical detector to thereby detect separation of the aqueous and oil phases of the wellbore fluid; and
      based upon the detected phase separation, evaluating the performance of the demulsifying agent.

9. The optical system as defined in claim 8, wherein evaluating the performance of the demulsifying agent comprises determining one or more of:
   an amount of separated water;
   a clarity of the separated water;
   an interface angle which reflects a phase separation quality;
   a water recovery percentage; and
   a speed of the phase separation.

10. The optical system as defined in claim 8, wherein:
    the operations are performed before a wellbore completion operation; and
    the operations further comprise selecting a demulsifying agent for use in the wellbore completion operation based upon the performance evaluation.

11. The optical system as defined in claim 8, wherein the operations are performed in real-time using an optical device positioned at a wellbore, the optical device being positioned in-line of the wellbore such that the optical device receives flow back fluid from the wellbore.

12. The optical system as defined in claim 11, wherein the operations further comprise altering a chemical makeup of the demulsifying agent in real-time based upon the performance of the demulsifying agent.

13. The optical system as defined in claim 8, wherein the optical system is integrated into a Flow-to-Refinery system.

* * * * *

UNITED STATES PATENT AND TRADEMARK OFFICE
CERTIFICATE OF CORRECTION

PATENT NO. : 11,414,989 B2
APPLICATION NO. : 16/614586
DATED : August 16, 2022
INVENTOR(S) : Li Guo et al.

Page 1 of 1

It is certified that error appears in the above-identified patent and that said Letters Patent is hereby corrected as shown below:

In the Specification

Column 1, Line 7, change paragraph:
"The present application is an International Patent Application of U.S. Provisional Application No. 62/558,154, filed on Sep. 13, 2017, entitled "OPTICAL ANALYSIS OF WELLBORE FLUID DEMULSIFIERS," the benefit of which is claimed and the disclosure of which is incorporated herein by reference in its entirety."

To:
-- The present application is a U.S. National Stage Patent Application of International Patent Application No. PCT/US2018/045098, filed August 3, 2018, which claims priority to U.S. Provisional Application No. 62/558,154, filed on September 13, 2017, entitled "OPTICAL ANALYSIS OF WELLBORE FLUID DEMULSIFIERS," the benefit of which is claimed and the disclosures of which are incorporated herein by reference in their entirety. --

Signed and Sealed this
Twentieth Day of September, 2022

Katherine Kelly Vidal
*Director of the United States Patent and Trademark Office*